United States Patent
Geyer et al.

(10) Patent No.: US 9,901,748 B2
(45) Date of Patent: Feb. 27, 2018

(54) APPARATUS FOR TRANSMITTING SIGNALS TO THE EYE

(71) Applicant: Pocket Sky OG, Vienna (AT)

(72) Inventors: Michael Geyer, Vienna (AT); Mark Wallerberger, Vienna (AT)

(*) Notice: Subject to any disclaimer, the term of this patent is extended or adjusted under 35 U.S.C. 154(b) by 0 days.

(21) Appl. No.: 15/512,124

(22) PCT Filed: Sep. 9, 2015

(86) PCT No.: PCT/AT2015/050224
§ 371 (c)(1),
(2) Date: Mar. 17, 2017

(87) PCT Pub. No.: WO2016/049669
PCT Pub. Date: Apr. 7, 2016

(65) Prior Publication Data
US 2017/0274222 A1    Sep. 28, 2017

(30) Foreign Application Priority Data

Sep. 29, 2014    (AT) ............................... A 50694/2014

(51) Int. Cl.
*A61N 5/06*    (2006.01)
*A61M 21/00*    (2006.01)

(52) U.S. Cl.
CPC ............. *A61N 5/0618* (2013.01); *A61N 5/06* (2013.01); *A61N 5/062* (2013.01);
(Continued)

(58) Field of Classification Search
CPC ........ A61N 5/0618; A61N 5/062; A61N 5/06; A61M 2205/33; A61M 2205/05; A61M 2021/0044
See application file for complete search history.

(56) References Cited

U.S. PATENT DOCUMENTS

| | | | | |
|---|---|---|---|---|
| 5,805,267 A | * | 9/1998 | Goldman | A61N 5/0618 |
| | | | | 351/200 |
| 7,147,319 B2 | * | 12/2006 | Lin | A61M 21/00 |
| | | | | 351/158 |

(Continued)

FOREIGN PATENT DOCUMENTS

| EP | 1982747 B1 | 9/2010 |
|---|---|---|
| EP | 1642609 B1 | 10/2012 |

(Continued)

*Primary Examiner* — Brian Miller
(74) *Attorney, Agent, or Firm* — David Guerra

(57) ABSTRACT

A portable device for the optical signal transmission from and to the human eye, in which it is proposed that a rod-shaped housing (1) is provided, on the two end regions of which at least one emitter (3) and/or detector of electromagnetic waves is arranged and which has a holding clamp (2) in its middle region, wherein a power supply for the respective at least one emitter (3) and/or detector as well as a control unit (8), which is connected to the at least one emitter (3) and/or detector, are provided within the rod-shaped housing. The invention provides a portable device for the optical signal transmission from and to the human eye, which can be worn with a high wearing comfort in a discreet manner in the vicinity of the head and, and in particular allows the device to be worn in parallel with commercially available spectacles. Furthermore, the handling, storage and transport of corresponding devices are greatly facilitated.

11 Claims, 9 Drawing Sheets

Figure 1:
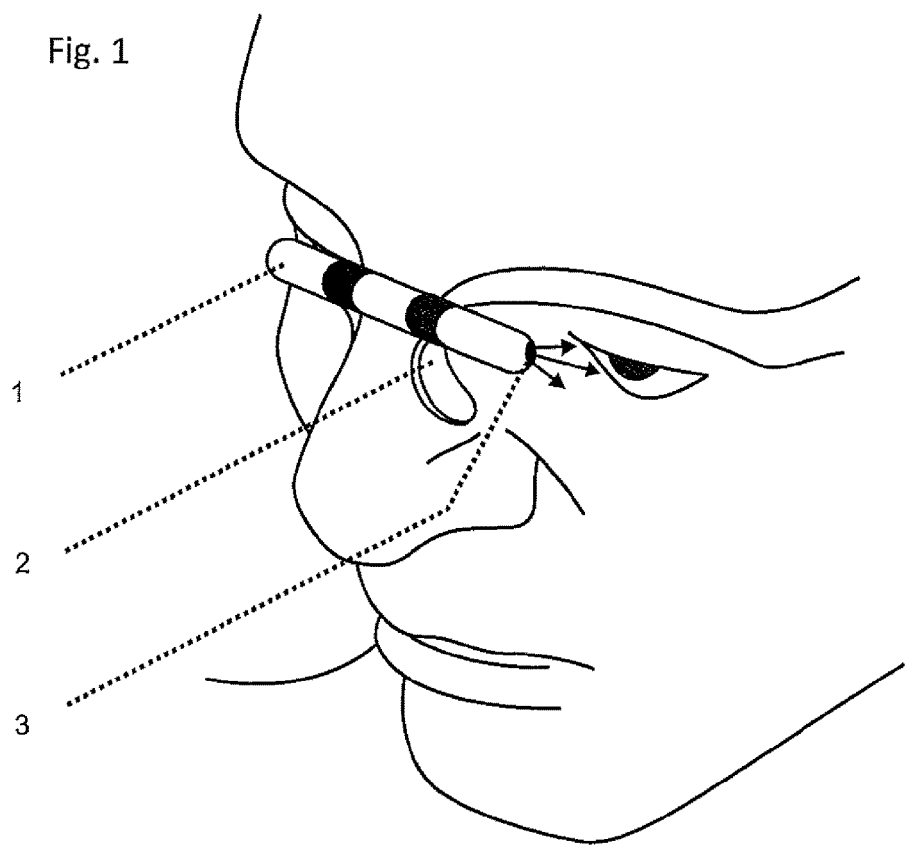

(52) U.S. Cl.
  CPC . *A61M 2021/0044* (2013.01); *A61M 2205/05* (2013.01); *A61M 2205/33* (2013.01)

(56) References Cited

U.S. PATENT DOCUMENTS

| | | | | |
|---|---|---|---|---|
| 8,715,328 B2* | 5/2014 | Gerardo | A61M 21/00 607/88 |
| 8,900,283 B2* | 12/2014 | Johnson | A61N 5/06 606/9 |
| 9,107,622 B2* | 8/2015 | Nistico | A61B 3/0008 |
| 9,248,309 B2* | 2/2016 | Pugh | A61M 21/02 |
| 9,798,153 B2* | 10/2017 | Ide | H04N 9/3129 |
| 2006/0259100 A1* | 11/2006 | Hilburg | A61N 5/0618 607/88 |
| 2011/0125230 A1* | 5/2011 | Friedman | A61N 5/0618 607/90 |
| 2012/0203310 A1* | 8/2012 | Pugh | A61M 21/00 607/93 |
| 2015/0209597 A1* | 7/2015 | Haarlander | A61N 5/0618 601/46 |
| 2016/0008568 A1* | 1/2016 | Attia | A61M 21/0094 600/28 |
| 2016/0106950 A1* | 4/2016 | Vasapollo | A61M 21/02 600/27 |
| 2016/0158485 A1* | 6/2016 | Givertz | A61M 21/00 607/90 |
| 2016/0167672 A1* | 6/2016 | Krueger | A61M 21/00 340/576 |
| 2016/0193442 A1* | 7/2016 | Adamczyk | A61M 21/02 600/27 |
| 2016/0270656 A1* | 9/2016 | Samec | A61B 3/085 |

FOREIGN PATENT DOCUMENTS

| | | |
|---|---|---|
| WO | 9315792 A1 | 8/1993 |
| WO | 2009118066 A1 | 10/2009 |
| WO | 2010076706 A1 | 7/2010 |
| WO | 2013124615 A1 | 8/2013 |
| WO | 2014020527 A2 | 2/2014 |

* cited by examiner

Fig. 12a    Fig. 12b    Fig. 12c
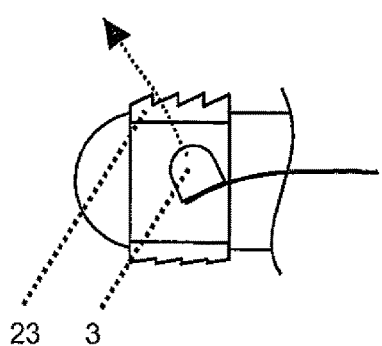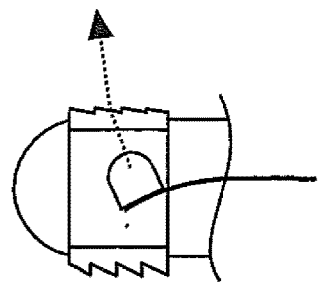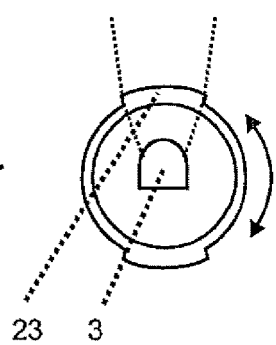
23  3        3          23  3
Fig. 13
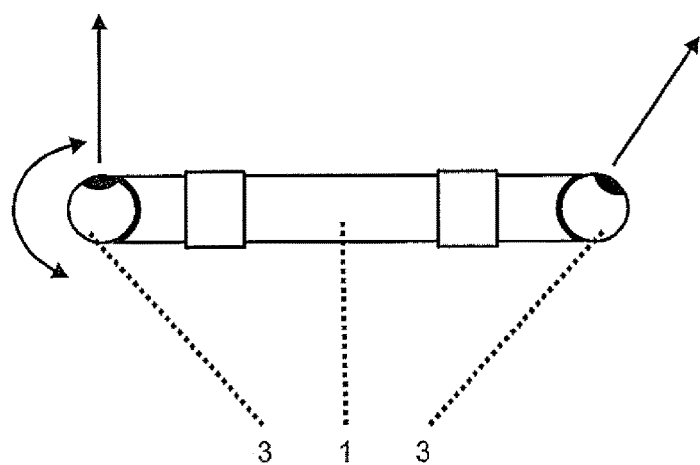
3   1   3
Fig. 14
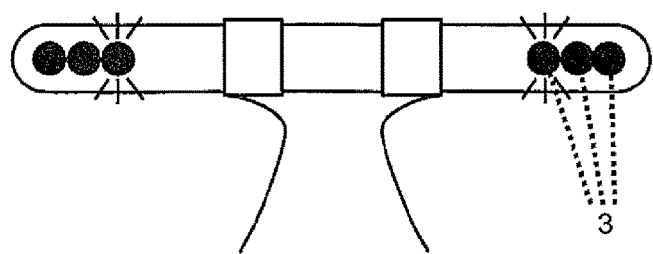
3

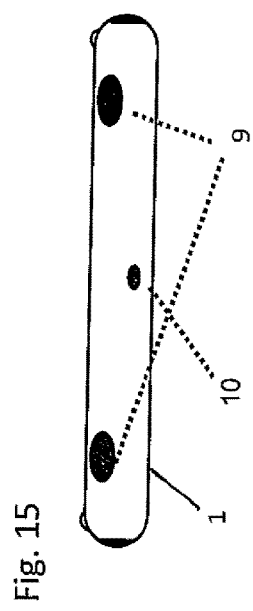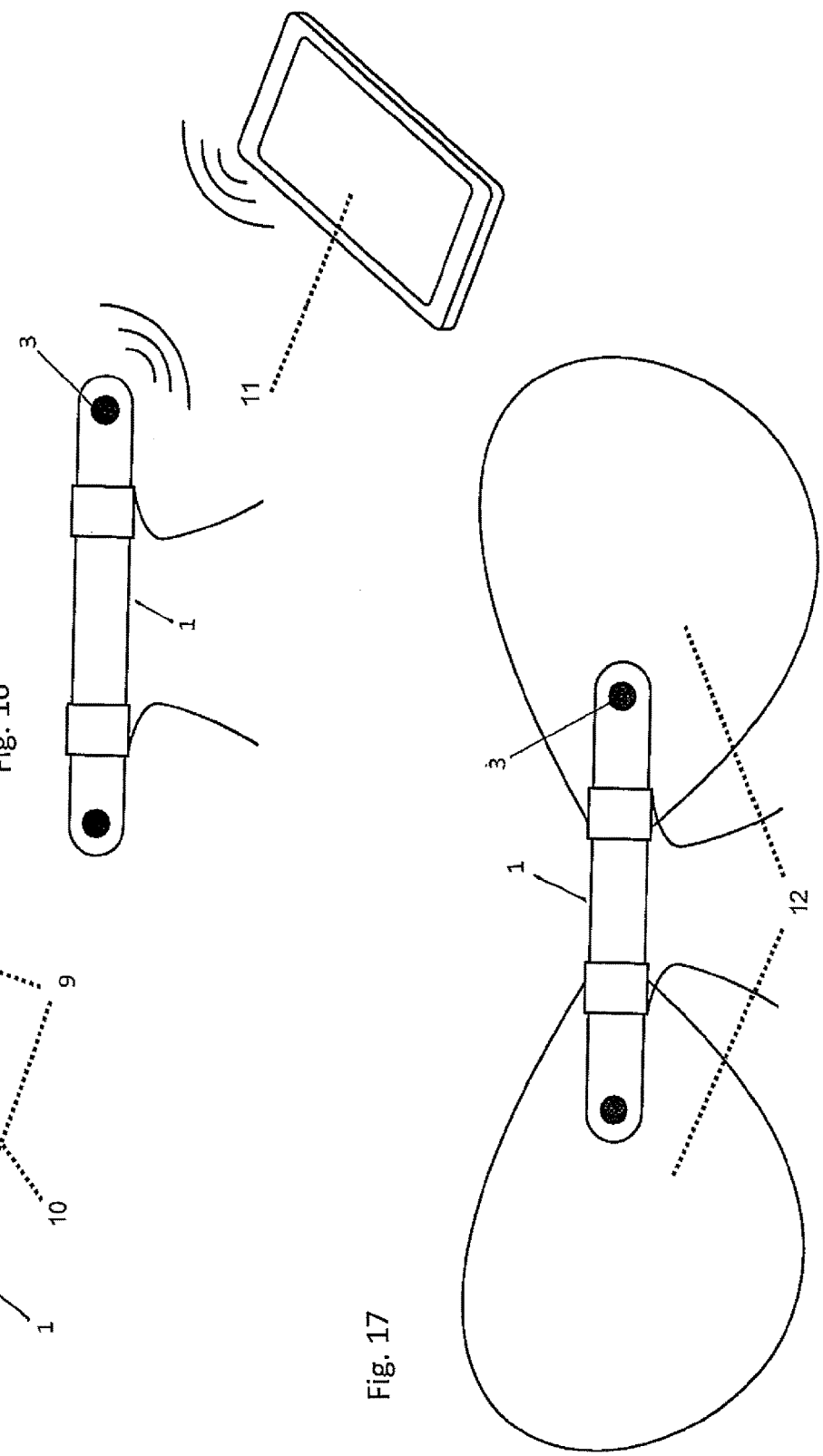

Fig. 18
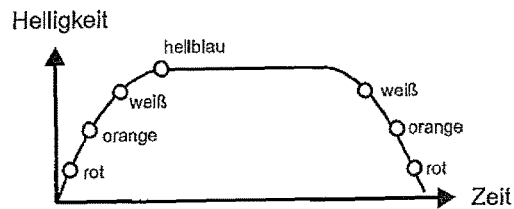
Fig. 19
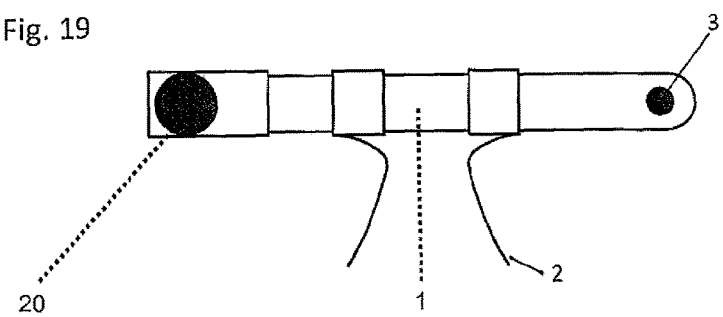
Fig. 20a     Fig. 20b
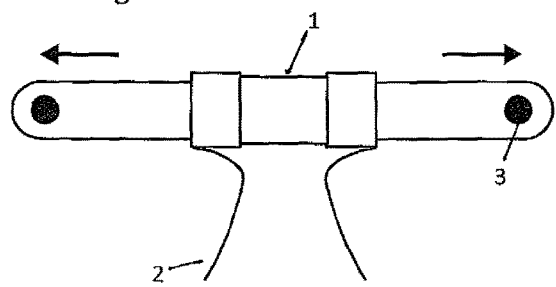 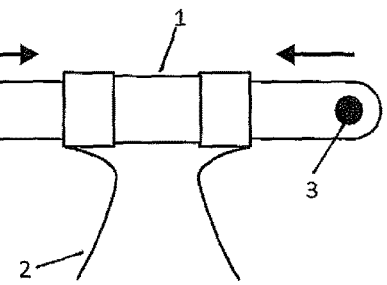
Fig. 21
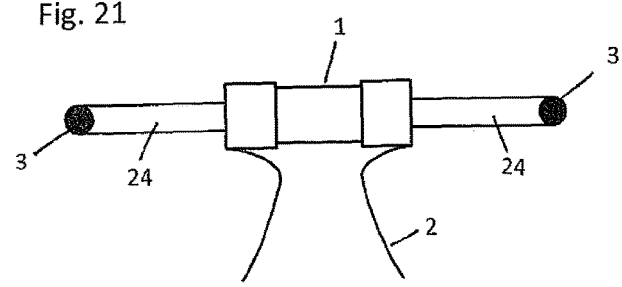

APPARATUS FOR TRANSMITTING SIGNALS TO THE EYE

The invention relates to a portable device for the optical signal transmission from and to the human eye according to the preamble of claim 1.

Such a device is to be used, in particular, for light therapy. Numerous disorders of the human condition are due to lack of light, especially in the blue frequency range. One of these disorders is known as "winter depression". In general, winter depression or seasonal affective disorder (SAD, Seasonal Affective Disorder) affects a depressive disorder in the autumn and winter months. In addition to the depressive symptoms, for example in the form of a depressed mood or reduction of the energy level and anxiety, also atypical symptoms such as prolongation of sleep duration, increased appetite for sweets, weight gain, increased suicide rate, increased accident frequency, etc. can occur.

These symptoms are due to the fact that in the normal case special ganglion cells in the retina react to blue light and suppress the release of melatonin. If this blue light component is missing due to a small amount of light in winter, various symptoms such as SAD syndrome may occur.

These symptoms can be combated by artificial intake of blue light. Blue light is proven to be therapeutically effective and not only affects seasonal depression, but also energy and light deficiency, jetlag, or premenstrual syndrome (PMS).

Therefore, various devices have already been proposed for artificially generating blue light and supplying it to the human eye. In most cases, these devices are designed as stationary devices, in front of which the person to be treated has to sit or lie. These devices therefore have the disadvantage that a therapy carried out with them is difficult to integrate into everyday life. Instead, preference should be given to devices that do not require any restrictions on everyday activities. For this purpose, devices which can be worn on the head have been proposed in WO 2009/118066 A1, WO 93/15792 A1, WO 2013/124615 A1, EP 1 642 609 A1 and WO 2010/076706 A1. Further devices have been described in EP 1982747 A1 and WO 2014/020527 A2.

It is therefore the object of the invention to provide a portable device for the optical signal transmission from and to the human eye, which can be worn with a high wearing comfort in an inconspicuous manner in the vicinity of the head and, in particular, allows uniform wearing of the device with commercially available spectacles. Furthermore, the handling, storage and transport of corresponding devices are to be facilitated.

These objects are achieved by the features of claim 1. Claim 1 relates to a portable device for the optical signal transmission from and to the human eye with at least one emitter and/or detector of electromagnetic waves, a power supply for the respective at least one emitter and/or detector and a control unit which is connected to the at least one emitter, wherein the at least one emitter and/or detector of electromagnetic waves are arranged at the two end regions of a rod-shaped housing which has a holding clamp in its middle region, and the power supply for the respective at least one emitter and/or detector, as well as the control unit, which is connected to the at least one emitter and/or detector, are arranged within the rod-shaped housing.

The device according to the invention is placed in the operating position in the user's nasal root region, whereby it can either be clamped directly onto the nose by means of the holding clamp or at the center of a spectacle. Owing to the small dimensions and the low weight of the device according to the invention, only small forces occur during head movements, so that the device is held sufficiently securely against the head by the holding clamps. The retaining clamp may also have a rubber-like coating or the like for improving the clamping fit. Furthermore, the clamping limbs of the retaining clamp can also be adjustable in their spacing relative to one another for adaptation to the respective nose shape. At least one emitter and/or detector of electromagnetic waves is arranged at the two end regions of the rod-shaped housing, which emitter and/or detector is directed in the direction of use of the user's eyes. The emitter in question is, in particular, a light source for emitting light in the visible spectral range, which emits the generated light directly into the respective eye of the user. In a cost-effective variant, for example, blue LEDs can be used which are suitable for light-therapeutic purposes and are already equipped with a corresponding bundling lens. In a more elaborate variant, however, it is also possible to use RGB LEDs which can also emit the therapeutic blue light, but in addition also have red and green spectral regions and thus, together with the blue light, can generate any light colors. In the following, an emitter is understood to mean an active emitter, in other words an emitter, which generates and emits electromagnetic waves instead of merely reflecting them. The generation of the electromagnetic waves and their emission from the rod-shaped housing may also take place locally separately from one another, for example by means of a light wave generator arranged within the rod-shaped housing, which is optically connected to the emitters arranged in the end regions which outcouple the light generated within the rod- Rod-shaped housing. However, also a display such as an LED display, which for example is used for biofeedback purposes, is also referred to as an emitter. The detector can be, for example, a brightness sensor or a camera in order to measure the brightness of the ambient light and, depending on the measured brightness, to control the intensity of the light emitted by the emitter. However, the detector can also be, for example, a sensor for the eye movements or pupil changes of the user in order to obtain conclusions for a therapeutically optimized control of the emitters.

The simple construction of the device according to the invention is particularly suitable for individual adaptation to the respective user. Preferably, the rod-shaped housing is rotatable relative to the retaining clamp about its longitudinal axis. In this way, the angle of the optical axis of the emitter and/or detector can be adjusted to a horizontal plane. In addition, it can be provided that the at least one emitter and/or detector can be rotated or pivoted relative to the rod-shaped housing about a rotational axis which is perpendicular to the longitudinal axis of the rod-shaped housing. In this way, the angle of the optical axis of the emitter and/or detector can be adjusted to a vertical plane. Furthermore, it can be provided that the rod-shaped housing is adjustable in length in order to be able to adjust it to different eye distances.

According to a preferred embodiment, the at least one emitter is a light source or light source group. The use of a light source group has several advantages. For example, the light intensity of the individual light sources can be reduced and the total light intensity distributed over a larger area in order to avoid a dazzling effect. On the other hand, it is also possible, by controlling individual light sources, to adapt to different eye spacings without requiring a length-adjustable housing of the rod-shaped housing. In particular for such an application, it is advantageous to arrange within the bar-shaped housing a control unit which is connected to the at least one emitter and/or detector, the light sources of a light source group being independently controllable by the control unit. With the aid of such a control unit, however, it is also possible not to adjust the light sources immediately after switching on to a maximum luminous intensity, but to perform a brightness increase similar to a sunrise, accompanied by a corresponding color change from orange red to yellow and white and blue. The same applies to the switch-off phase, where a sunset can be simulated.

For more complex control programs of this type, it is advantageous if the rod-shaped housing can be connected to an external device via a wireless connection. In this way, the control unit can be connected to an external device, preferably a mobile telephone, by means of a wireless connection in order to outsource computing power to the external device and to enable simple graphical user guidance, for example for selecting color variants, light emission sequences or a user-defined, time-controlled light emission. The status of the device according to the invention can also be displayed on the external device, e.g. the charging state of the power supply. Furthermore, the device according to the invention can thus also become the subject of appropriately specialized application software of mobile devices ("Apps").

A plurality of optical devices is available for the optimization of the signal transmission between the emitter and/or the detector and the user's eye. For example, Fresnel lenses can be arranged in the end regions of the rod-shaped housing in order to form the emission profile of light sources, wherein the emitter can also be displaceable relative to the associated Fresnel lens in order to generate additional emission profiles. In a preferred embodiment, the rod-shaped housing can be provided with a plug-on sleeve which has optical elements for shaping the radiation angle and/or brightness of the emitter.

Figure 2:
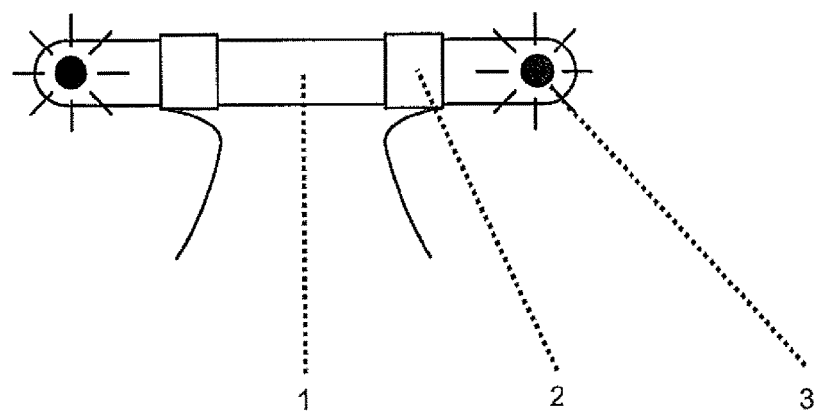
Figure 3:
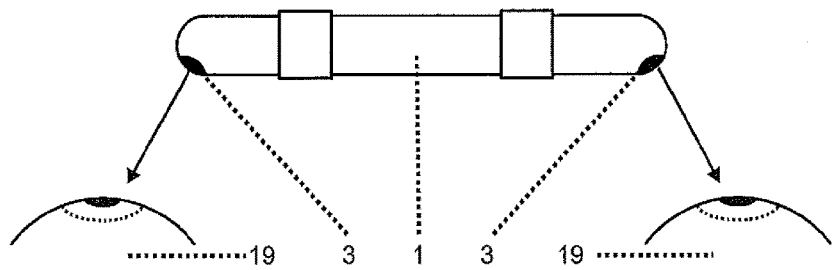
Figure 6A:
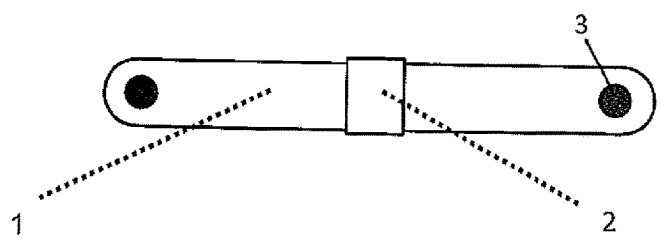
Figure 6B:
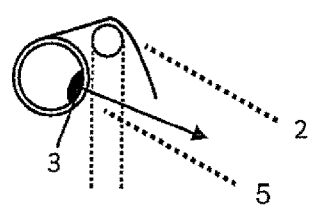
Figure 7:
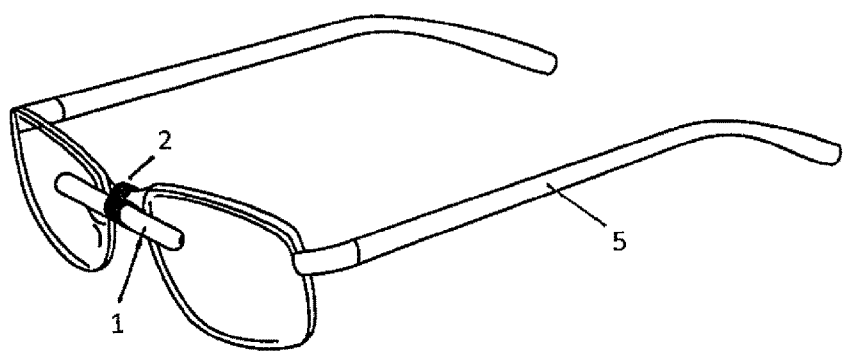
Figure 8:
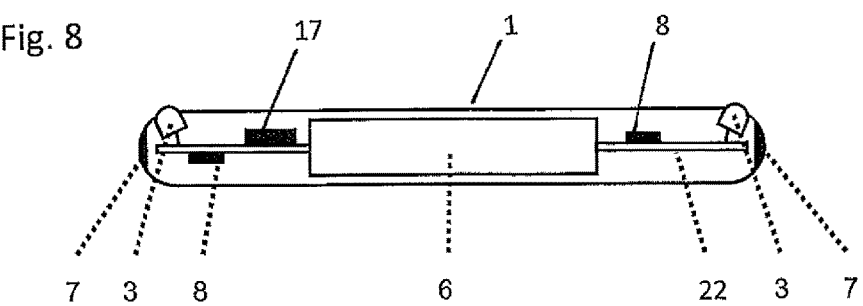
Figure 9A:
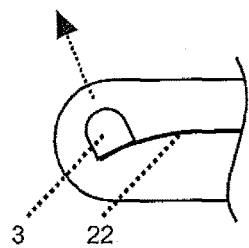
Figure 9B:
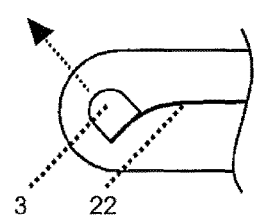
Figure 10A:
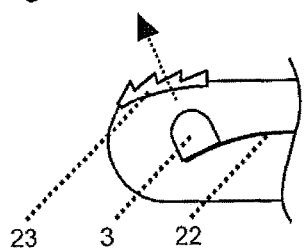
Figure 10B:
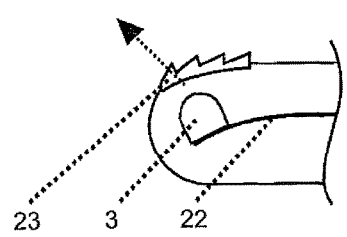
Figure 11A:
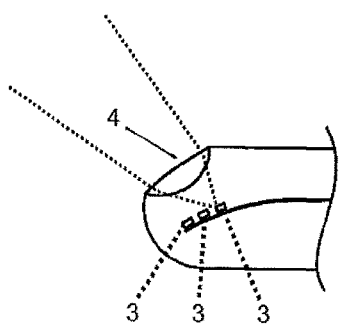
Figure 11B:
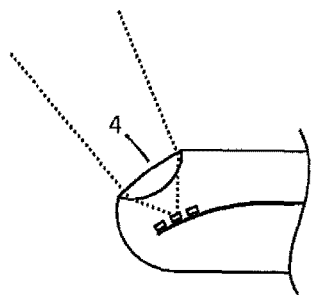
Figure 11C:
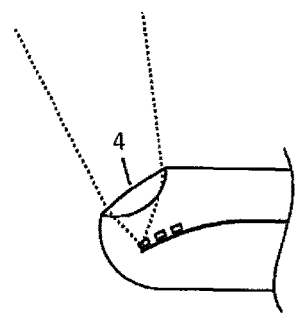
Figure 22A:
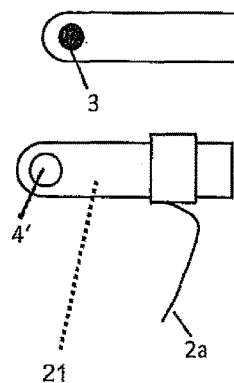
Figure 22B:
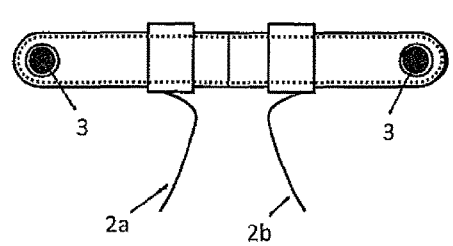
Figure 23A:
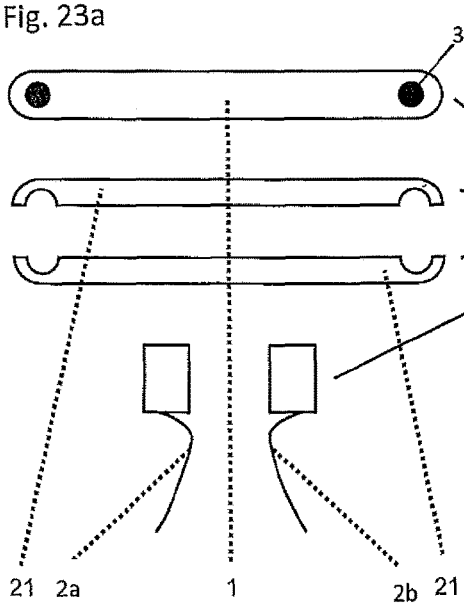
Figure 23B:
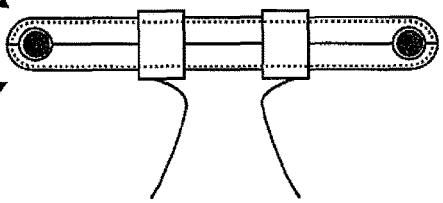
Figure 24:
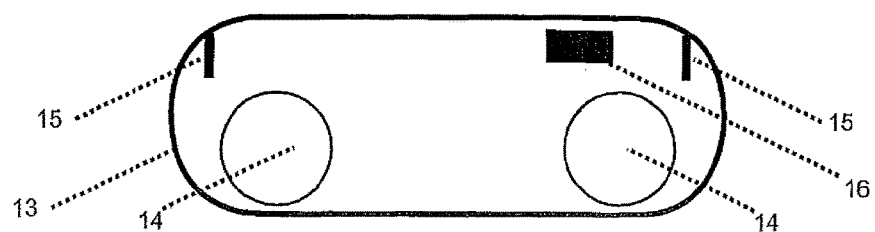
Figure 25:
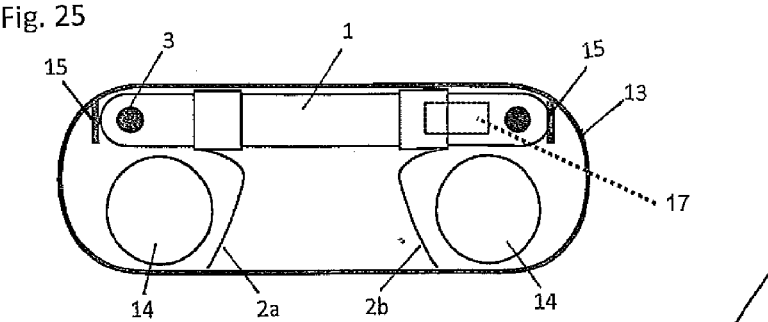
Figure 26:
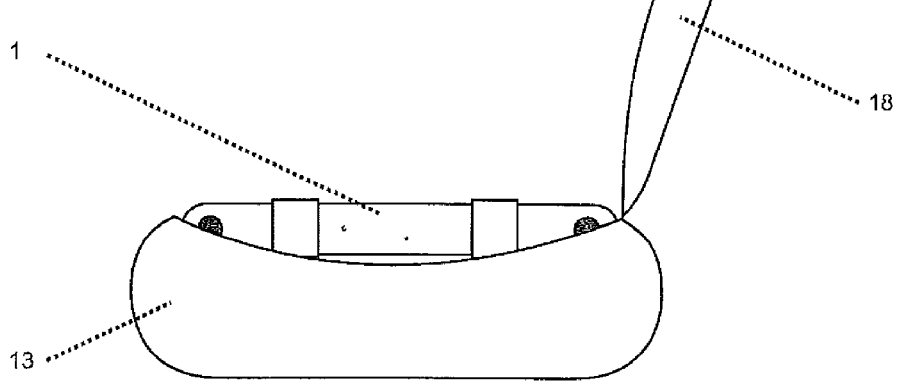
Figure 27:
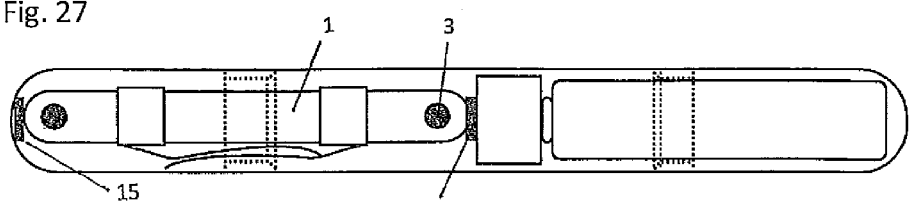
Figure 28:
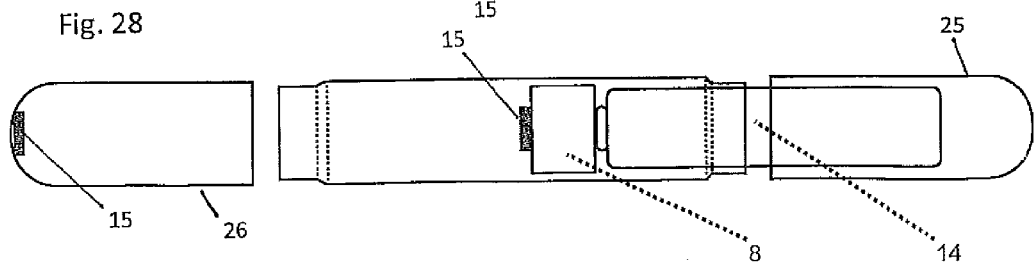

The invention will be explained in more detail below with reference to exemplary embodiments with the aid of the appended figures. Here, the FIG. 1 shows a perspective view of an embodiment of the device according to the invention in the position of use, FIG. 2 shows a view of an embodiment of the recommended device from the user perspective, FIG. 3 shows a view of an embodiment of the recommended device viewed from above with the main beam direction of the emitters indicated by arrows, FIGS. 4a and 4b show views of an embodiment of the recommended device, each with a different spacing between the clamping limbs of the retaining clamp viewed by the user FIGS. 5a and 5b show lateral views of an embodiment of the device according to the invention in the case of a different rotational position of the rod-shaped housing relative to the retaining clamp, FIG. 6a shows a view of a further embodiment of the recommended device for fastening to a pair of spectacles viewed from the user, FIG. 6b shows a side view of the embodiment fastened to a pair of spectacles according to FIG. 6a, FIG. 7 shows a perspective view of the embodiment fastened to a spectacle according to FIG. 6, FIG. 8 shows a sectional view of an embodiment of the recommended device with emitter, power supply, control unit and charging contacts, FIGS. 9a and 9b show detailed views of two emission positions of an emitter arranged at the end of a flexible circuit board, FIGS. 10a and 10b show detailed views of two emission positions of an emitter arranged on one side, which is arranged such that it can be displaced relative to a Fresnel lens, FIGS. 11a-11c show detailed views of different radiation angles of an emitter arranged in the form of a light source group and arranged at the end by controlling different light sources of the light source group, FIGS. 12a and 12b show different emission angles of an emitter arranged at the end, as a result of different rotational positions of a Fresnel lens designed in the form of a sleeve, perpendicular to the longitudinal axis of the rod-shaped housing, FIG. 12c shows the embodiment according to FIGS. 12a and 12b in the longitudinal direction of the rod-shaped housing, FIG. 13 shows a view of a further embodiment of the recommended device with an emitter which is designed so as to be pivotable relative to the rod-shaped housing, viewed from above, FIG. 14 shows a view of a further embodiment of the recommended device with two emitters, each configured as a light source group, viewed from the user, FIG. 15 shows a further embodiment of the device according to the invention with additional cameras and brightness sensors as viewed from above, FIG. 16 shows a further embodiment of the device according to the invention in data connection with an external device, FIG. 17 shows a further embodiment of the apparatus according to the invention with two filter discs arranged on both sides, viewed from the user, FIG. 18 shows a possible light color curve for simulating a sunrise and sunset, FIG. 19 shows a further embodiment of the device according to the invention with an optical plug-on sleeve, viewed from the user, FIGS. 20a and 20b show a further embodiment of the apparatus according to the invention with a length-adjustable housing at two different longitudinal positions viewed from the user, FIG. 21 shows a further embodiment of the device according to the invention with thin side supports as viewed from the user, FIG. 22a shows a further embodiment of the apparatus according to the invention with plug-on sleeves in the disassembled state, FIG. 22b shows the embodiment according to FIG. 22a in the assembled state, FIG. 23a shows a further embodiment of the device according to the invention with plug-on sleeves in the dismantled state, FIG. 23b shows the embodiment according to FIG. 23a in the assembled state, FIG. 24 shows an embodiment of a storage and charging container with charging contacts, magnet and current sources, FIG. 25 shows the storage and charging container according to FIG. 24 with inserted device according to the invention, FIG. 26 shows the storage and charging container according to FIGS. 24 and 25 with inserted device according to the invention in the open state, FIG. 27 shows a further embodiment of a storage and charging container for the device according to the invention, and FIG. 28 shows the storage and charging container according to FIG. 27 in the open state.

FIG. 1 shows a perspective view of an embodiment of the device according to the invention in the position of use, the rod-shaped housing 1 being fastened to the user's nose by means of the holding clamp 2. The holding clamp 2 is designed in the form of two preferably resilient clamping limbs 2a, 2b. An emitter 3 and/or detector are arranged at each end region of the rod-shaped housing 1. In the exemplary embodiment shown, the light source, for example, is a light source which emits visible light into the eyes of the user. FIG. 2 shows a view of the embodiment of the device according to the invention according to FIG. 1, viewed from the user, and FIG. 3 shows a view of this embodiment of the device according to the invention viewed from above with the main beam direction of the emitters 3 indicated by arrows. It can be seen here that an eye of the user is assigned to each of the two emitters 3 and the main beam direction of the emitter 3 is to be aligned in such a way that the best possible emission of the light into the respective associated eye 19 of the user takes place. The main directions of the rays are indicated by arrows in FIG. 3.

Figure 4A:
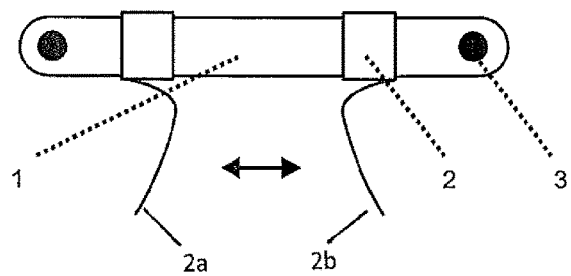
Figure 4B:
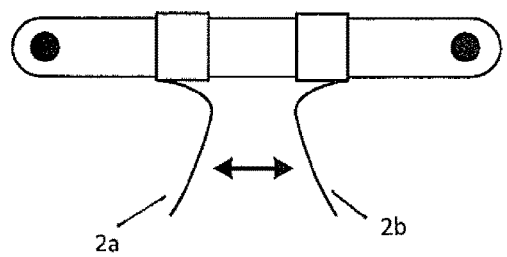

In order to optimize the clamping fit of the holding clamp 2 on the user's nose, it can be provided that the two clamping limbs 2a, 2b of the holding clamp 2 are adjustable in their distance from one another, as shown in FIG. 4. FIGS. 4a and 4b show views with different distances, respectively, from the clamping limbs 2a, 2b of the holding clamp 2 as viewed by the user.

Figure 5A:
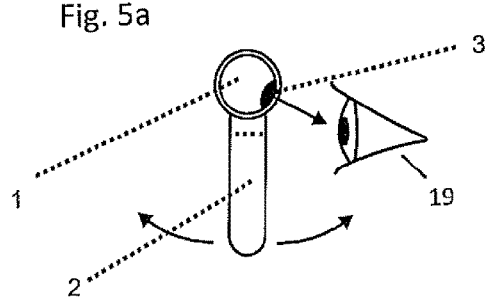
Figure 5B:
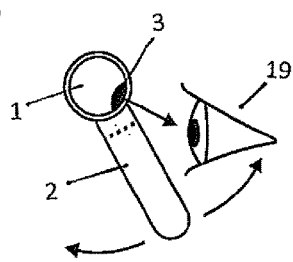

In order to be able to adjust the angle of the optical axis of the emitter 3 relative to a horizontal plane, the rod-shaped housing 1 can be made rotatable relative to the holding clamp 2 about the longitudinal axis of the rod-shaped housing 1, as shown in FIG. 5. FIGS. 5a and 5b show lateral views of this embodiment of the device according to the invention in the case of a different rotational position of the rod-shaped housing 1 relative to the holding clamp 2, the rectilinear arrows indicating the main beam direction of an emitter 3, and the curved arrows indicating the rotational directions of the holding clamp 2 relative to the rod-Housing 1.

The device according to the invention can also be attached to a pair of spectacles 5, as shown in FIGS. 6 and 7. For this purpose, the holding clamp 2 can be embodied correspondingly, for example in the form of a retaining bracket, as can be seen in FIG. 6b. Since in any case a minimum clamping force is required for the secure fastening to the spectacles 5, an embodiment similar to a holding bracket is also referred to as a retaining clamp 2. FIG. 6 a shows a view of such an embodiment from the user, and FIG. 6b shows a side view. FIG. 7 shows a perspective view of the embodiment fastened to a pair of spectacles 5 according to FIG. 6.

A possible construction of a device according to the invention is explained with reference to FIG. 8. Inside the rod-shaped housing 1, a power supply 6 is arranged, which is connected in a conductive manner to charging contacts 7, which are each located at the two ends of the rod-shaped housing 1. Furthermore, a control unit 8 is provided for the emitter 3 and/or detector within the rod-shaped housing 1, wherein in the exemplary embodiment shown each of the two emitters 3 is controlled with its own control unit 8. An emitter 3 is arranged in each of the two end regions of the rod-shaped housing 1, in the exemplary embodiment shown represented by a LED lamp. Furthermore, a magnet sensor 17 can also be provided within the rod-shaped housing 1, the function of which will be explained in more detail below.

The emitter 3 and/or detector can in each case be connected via a circuit board 22 to the power supply 6 and the control unit 8 assigned to them in each case, which can also be designed to be flexible. The flexible design also has the advantage that the radiation angle of the emitters 3 can be changed as explained with reference to FIG. 9. FIGS. 9a and 9b show detailed views of two emission positions of an emitter 3 arranged on the end side on a flexible circuit board 22, wherein the angle of the main beam direction of the relevant emitter 3 relative to a vertical plane can be changed depending on the bending position of the circuit board 22.

Of course, the main beam direction of the emitters 3 can also be changed by means of optical devices. FIG. 10 shows an example by means of a Fresnel lens 23, which is arranged in the two end regions of the rod-shaped housing 1 in the emission region of the respective emitter 3. FIGS. 10a and 10b show detailed views of two emission positions of an emitter 3 arranged at the end, which is arranged displaceably relative to the Fresnel lens 23 assigned to it. The position of the emitter 3 can be adjusted at the factory or can be carried out by means of displacement mechanisms from the outside.

A further possibility for changing the main directions of the emitters 3 is shown in FIG. 11. FIGS. 11a-11c show detailed views of different emission angles of three emitters 3 arranged in the form of a light source group, arranged at the end, by controlling different emitters 3 of the light source group. The appropriate control of the light source group is effected via the control unit 8. The different main beam direction is thereby obtained by a different positioning of the selected emitter 3 of the light source group relative to a radiation opening 4 in the rod-shaped housing 1, which is arranged in the emission region of the emitter 3.

FIG. 12 shows an embodiment similar to that shown in FIG. 10, wherein different emission angles of an emitter 3 arranged at the end are brought about due to different rotational positions of a Fresnel lens 23 formed in the form of a sleeve, the Fresnel lens 23 being shaped like a sleeve being rotatable about the longitudinal axis of the rod-shaped housing 1. The twistability is clearly shown in FIG. 12c, which shows this embodiment as seen in the longitudinal direction of the rod-shaped housing 1 according to FIGS. 12a and 12b. The curved arrows indicate the rotational directions of the sleeve-shaped Fresnel lens 23, which is manufactured in its peripheral region with different optical properties. Depending on which peripheral section is located in the radiation aperture 4 of the relevant emitter 3, the main beam direction of the radiated light will have different orientations, as indicated by the curved arrows in FIGS. 12a and 12b.

A further possibility for changing the main radiation directions of the emitters 3 is shown in FIG. 13. In this case, the end-mounted emitters 3 are designed to be pivotable relative to the rod-shaped housing 1, the pivot axis being oriented perpendicular to the longitudinal axis of the rod-shaped housing 1. The main directions of the emitters 3 are indicated by rectilinear arrows and the pivoting direction by curved arrows.

FIG. 14 shows a view of a further embodiment of the device according to the invention with two emitters 3 each configured as light source groups. By means of such an embodiment, on the one hand, an adjustment to different eye distances can be made by activating one of the light sources of each light source group or, on the other hand, reducing the light intensity of each emitter 3 if all emitters 3 of a light source group are activated. In the latter case, a glare effect on the user can be avoided.

The device according to the invention is also suitable as a carrier for additional components, the arrangement of which can be advantageous in close proximity to the eyes and support the activity of the emitters 3 and/or detectors. FIG. 15 shows an embodiment of the device according to the invention with additional cameras 9 and a brightness sensor 10. The cameras 9 can be used, for example, to detect eye movements or changes in the pupils of the user. The brightness sensor 10 detects the ambient light intensity and, if necessary, reduces the light intensity of the emitters 3 in order not to exceed a predetermined total light intensity on the eyes of the user.

Owing to the various operating possibilities of the device according to the invention, it can be expedient to swap out the operation and control of the components within the rod-shaped housing 1 to an external device 11, as can be seen from FIG. 16. The external device 11 can be, for example, a mobile telephone which can be connected by means of a wireless connection to an operating interface of the rod-shaped housing 1.

FIG. 17 shows a further application of the device according to the invention in which the rod-shaped housing 1 is provided with two filter discs 12 which can be fitted on both sides. These filter discs 12 can be, for example, color-toned plastic films which have an orange color in order to filter off the blue light coming from the outside. This achieves the opposite effect of the blue light, namely activation of melatonin, as a result of which adverse effects of a "jet lag" can be avoided.

FIG. 18 shows a possible course of the brightness of the light of the emitters 3 as a function of time. It can be seen that after starting the device, for example, a gradual increase in the light intensity and a change in the light color from red over orange and yellow to the final blue light, or blueish white light can take place to simulate a sunrise. Similarly, this process can be reversed when the device is turned off to simulate a sunset. The simulation of a sunrise or sunset can be accomplished, for example, with a plurality of different color emitters 3 (red, green and blue).

FIG. 19 shows a further embodiment of the apparatus according to the invention with an optical plug-on sleeve 20. In the embodiment shown, the plug-in sleeve 20 is slipped outwards from the outside in the direction of the longitudinal axis of the rod-shaped housing 1 and covers the radiation opening 4 of the respective emitter 3 in the pushed-on state. The plug-on sleeve 20 thereby changes the emission characteristics of the emitters 3 by acting, for example, as a diffuser or expanding the angle of the emitted light of the emitter 3 in question.

A further possibility for adapting the device according to the invention to different eye spacings is shown in FIG. 20, in that the rod-shaped housing 1 is of length-adjustable design. FIGS. 20 *a* and 20*b* show two different longitudinal positions of the rod-shaped housing 1, which can be implemented, for example, by a pull-out mechanism in the direction of the arrows shown.

A particularly slim and elegant embodiment is shown in FIG. 21, in which the emitter 3 and/or detectors arranged at the ends are arranged on thin side supports 24 of the rod-shaped housing 1. In this case, the rod-shaped housing 1 has a central region to which the holding clamp 2 is fastened, as well as two end regions, which are embodied in the form of the two side carriers 24. This embodiment is particularly suitable for a length adjustability of the entire arrangement in that the side carriers 24 of the rod-shaped housing 1 can be pushed in and out relative to the central region.

FIG. 22 shows a further embodiment of the apparatus according to the invention, in which the rod-shaped housing 1 can be provided with sleeves 21 which can be fitted on both sides on its end regions in the longitudinal direction of the rod-shaped housing 1. 22*a* shows the rod-shaped housing 1 and the sleeves 21 in the disassembled state, and FIG. 22*b* shows the embodiment according to FIG. 22*a* in the mounted state. The sleeves 21 in each case have a radiation opening 4', which is aligned with the radiation opening 4 of the rod-shaped housing 1 in the assembled state. The sleeves 21 furthermore each support one of the clamping limbs 2*a*, 2*b*, so that they form the holding clamp 2 in the mounted state. This embodiment has the advantage that the sleeves 21 can be replaced in the case of wear or damage and protect the rod-shaped housing 1.

FIG. 23*a* shows a further embodiment of the device according to the invention with plug-on sleeves 21 in the disassembled state, and FIG. 23*b* shows the embodiment according to FIG. 23*a* in the mounted state. The sleeve 21 is constructed in the form of two clamping members which receive the rod-shaped housing 1 in the transverse direction thereof. Subsequently, fastening sleeves for a respective clamping limb 2*a*, 2*b* can be slipped onto the mounted sleeve 21, which in turn again form the holding clamp 2 in the mounted state.

FIGS. 24-26 show an embodiment of a storage and charging container 13 for the device according to the invention. The storage and charging container 13 is provided with current sources 14, which are in conductive connection with charging contacts 15. The current sources 14 can be designed, for example, as charging batteries. Alternatively, the current sources 14 can also be designed as a rechargeable battery, which can be charged via a separate charging electronics via a USB connection, for example. As shown in FIG. 25, the charging contacts 7 of the rod-shaped housing 1 (see FIG. 8) are in electrical contact with the charging contacts 15 as soon as the device according to the invention has been inserted into the storage and charging container 13. Furthermore, the storage and charging container 13 can be provided with a magnet 16, which, when the housing 1 is inserted, comes to lie close to the magnet sensor 17, which is arranged within the rod-shaped housing 1. The control unit 8 located within the rod-shaped housing 1 can thus detect whether the device according to the invention has been inserted into the storage and charging container 13 and, as a result, opens a charging circuit for the power supply 6. The device according to the invention can, however, also recognize whether it has been removed from the storage and charging container 13 and followingly start with a lighting cycle or also terminate it as soon as it has been inserted into the storage and charging container 13. FIG. 26 shows the storage and charging container 13 according to FIGS. 24 and 25 with inserted device according to the invention with the lid 18 of the storage and charging container 13 open. The storage and charging container 13 can be designed to be very compact and can therefore be carried along at any time easily and unobtrusively by the user.

FIGS. 27 and 28 show a further embodiment of a storage and charging container 13 for the device according to the invention. FIG. 27 shows the storage and charging container 13 with inserted device according to the invention and FIG. 28 the storage and charging container 13 according to FIG. 27 in the open state without the device according to the invention. This embodiment of the storage and charging container 13 also has two charging contacts 15, a charging contact 15 being arranged in a plug-on charging sleeve 4, which can be plugged onto a central part of the storage and charging container 13. Furthermore, a further sleeve 25, which protects approximately a micro-USB connection, can be plugged onto the opposite end of the storage and charging container 13. Furthermore, a current source 14 is provided, which is in conductive connection with the charging contacts 15. If the device according to the invention is inserted into the storage and charging container 13 and the charging sleeve 4 has been slipped on, the charging contacts 7 of the rod-shaped housing 1 are in electrical contact with the charging contacts 15. Also in this case, the storage and charging container 13 can be provided with a charging contact (not shown in FIGS. 27 and 28) which, when the housing 1 is inserted, comes to lie close to the magnet sensor 17, which is arranged within the rod-shaped housing 1. The control unit 8 located within the rod-shaped housing 1 can thus again detect whether the device according to the invention has been inserted into the storage and charging container 13 and subsequently open a charging circuit for the power supply 6.

The portable device according to the invention can thus be implemented very compact, whereby also very practical storage and charging containers 13 are proposed. The invention provides a portable device for the optical signal transmission from and to the human eye, which can be worn with a high wearing comfort in a discreet manner in the vicinity of the head and, in particular, allows the device to be worn in parallel with commercially available spectacles. Furthermore, the handling, storage and transport of corresponding devices are greatly facilitated.

REFERENCE LIST 1 rod-shaped housing
2 holding clamp
3 emitters
4 radiation opening
5 glasses
6 power supply
7 charging contacts
8 control unit
9 camera
10 brightness sensor
11 external device
12 plug-in filter discs
13 storage and charging containers
14 power source
15 charging contacts
16 magnet
17 magnet sensor
18 cover
19 eye
20 optical plug-on sleeve
21 case
22 board
23 fresnel lens
24 side carriers
25 sleeve
26 charging sleeve

The invention claimed is:

1. A portable device for optical signal transmission from and to a human eye, the portable device comprising:
a rod shaped housing having at least two end regions, and a holding clamp in a middle region of the rod shaped housing;
at least two emitters and/or detectors of electromagnetic waves, at least one of the emitters and/or detectors being arranged at each of the two end regions of the rod shaped housing;
a power supply for at least the emitters and/or detectors; and
a control unit connected to and in communication with the emitters and/or detectors;
wherein the power supply as well as the control unit are arranged within the rod-shaped housing.

2. The portable device according to claim 1, wherein the rod-shaped housing is rotatable about its longitudinal axis relative to the holding clamp.

3. The portable device as claimed in claim 1, wherein each of the emitters and/or detectors are rotatable or pivotable rotated or pivoted relative to the rod-shaped housing about a rotational axis perpendicular to the longitudinal axis of the rod-shaped housing.

4. The portable device according to claim 1, wherein the rod-shaped housing is adjustable in length.

5. The portable device as claimed in claim 1, wherein each of the emitters and/or detectors is a light source or light source group.

6. The portable device according to claim 5, wherein the at least one emitter and/or detector is a light source group including light sources controlled independently of one another by the control unit.

7. The portable device as according to claim 1, wherein the rod-shaped housing is connectable to an external device by way of a wireless connection.

8. The portable device as according to claim 1, wherein the rod-shaped housing is provided with a plug-on sleeve which has optical elements for shaping the radiation angle and/or brightness of the emitters and/or detectors.

9. The portable device according to claim 1, wherein each of the emitters and/or detectors is configured to be aligned with an eye of a wearer of the portable device.

10. The portable device according to claim 1, wherein the holding clamp has a configuration capable of clamping to one selected from the group consisting of a nose of a wearer of the portable device, a head of the wearer, and a spectacle.

11. The portable device according to claim 1, wherein an orientation of each of the emitters and/or detectors is adjusted by one selected from the group consisting of a flexible circuit board fitted with the emitters and/or detectors, and at least one Fresnel lens located at the two end regions of the rod shaped housing and aligned with each of the emitters and/or detectors respectively.

* * * * *